United States Patent [19]

Blackman

[11] Patent Number: 4,873,265

[45] Date of Patent: Oct. 10, 1989

[54] ANTI-INFECTIVE METHODS AND COMPOSITIONS

[75] Inventor: Steven T. Blackman, New York, N.Y.

[73] Assignee: Thames Pharmacal Co., Inc., Rokonkoma, N.Y.

[21] Appl. No.: 218,956

[22] Filed: Jul. 14, 1988

[51] Int. Cl.$^4$ .................... A61K 31/135; A61K 31/52
[52] U.S. Cl. ..................................... 514/651; 514/263
[58] Field of Search ............................... 514/263, 651

[56] References Cited

PUBLICATIONS

Martindale Pharmacopoeia 28th Ed. 1982 p. 1311.
Facts & Comparisons 12/76 Product List for Antihist, Contg. Prep. Topical pp. 572–573.
Remington's Pharmaceutical Sciences 15th ed. 1975 pp. 1252–1253.
Chem. Abstracts 86(1):620c Antibacterial Activity of Ambodryl and Benadryl Jan. 3, 1977.
Chem Abstracts 86(11):66137g Antimicrobial Activity of Antihistaminic Drugs Mar. 14, 1977.
Chem. Abstracts 102(17):146020c In Vitro Activity of Ethanolamine- and Phenothiazine Derived and Aminoalkyl Antihistamines Against Some Selected Bacterial Strains 4/9/85.
Drug Evaluations 6th edition (American Medical Association) pp. 1503–1507.

Primary Examiner—Douglas W. Robinson
Assistant Examiner—Raymond J. Henley, III
Attorney, Agent, or Firm—Kirschstein, Ottinger, Israel & Schiffmiller

[57] ABSTRACT

Methods of providing local anti-infective treatment to a human or animal tissue area requiring such treatment comprise the application to the affected tissue area of an effetive amount of a composition containing from 0.5 to 5% by weight of selected antihistaminic agents in pharmaceutically acceptable topical vehicles including liquids, lotions, aerosols, creams, gels and ointments.

14 Claims, No Drawings

ANTI-INFECTIVE METHODS AND COMPOSITIONS

BACKGROUND OF THE INVENTION

1. Field of the Invention

The invention relates to methods of providing local anti-infective treatment to human or animal tissues and compositions useful in such treatments.

2. Description of the Prior Art

Local or topical antibacterial or antimycotic agents have been commercially available in a variety of preparations and vehicles for many years. Examples of the active ingredients commonly found in such locally applied antimicrobial compositions include bacitracin, polymyxin, neomycin, povidone iodine, benzoyl peroxide, tolnaftate, miconazole and the like. In addition, it is known that ethyl alcohol, which is utilized as a solvent or diluent in a number of topical antibacterial preparations, has significant bactericidal activity.

Antihistaminic agents, i.e., drugs capable of antagonizing the in vivo effects of histamine have been known for decades. The classical antihistamines act by competitively antagonizing the effects of histamine at H1-receptor sites. While antihistamines have traditionally been administered orally and in some instances parentally, topical antihistaminic preparations, particularly incorporating diphenhydramine, have been used to reduce pruritus caused by, e.g., fixed drug eruptions, contact dermatitis and insect bites. Such topical antihistaminic preparations have also been utilized to treat the erythema and edema of insect bites, poison ivy and so on.

In conditions where both local relief of pruritus and edema and anti-infective treatment are required, it has been conventional to apply both an antihistaminic agent and a topically effective antimicrobial agent to the affected area to achieve the desired therapeutic effects. It has not hitherto been disclosed that the use of a topically effective antihistaminic agent alone in a suitable topical vehicle would achieve any significant bactericidal, bacteriostatic and/or antimycotic effects.

SUMMARY OF THE INVENTION

It has now been discovered, surprisingly, that certain antihistaminic agents when incorporated into pharmaceutically acceptable topical vehicles, exhibit substantial and significant antimycotic and antibacterial activity, both bactericidal and bacteriostatic in nature, without the additional or concomitant use of any separate anti-infective or antimicrobial agent.

The subject invention comprehends methods of providing local anti-infective treatment to a human or animal tissue area comprising the application to said tissue area of a composition containing an effective concentration of certain antihistaminic agents together with a pharmaceutically acceptable topical vehicle, e.g., a pharmaceutically suitable and compatible liquid, lotion, aerosol, cream, gel or ointment. An effective amount of such a topical antihistamine-containing preparation may be applied one to five times daily to achieve the desired anti-infective effect as well as local antihistaminic activity.

DETAILED DESCRIPTION OF THE INVENTION

The methods of the present invention comprise the providing of local anti-infective treatment to a human or animal tissue area by applying to said tissue area an effective antibacterial or antimycotic (i.e., antifungal and anti-yeast) amount of a composition containing (a) from about 0.5 to about 5% by weight of antihistaminic agent selected from the group consisting of ethanolamine derivatives, ethylenediamine derivatives and alkylamine derivatives, as well as pharmaceutically acceptable salts thereof, and (b) a pharmaceutically acceptable topical vehicle selected from the group consisting of liquids, lotions, aerosols, creams, gels and ointments.

The term "ethanolamine derivatives" as used herein refers to antihistaminic compositions having structural formulas exemplified by, but not limited to, the following species;

Diphenhydramine

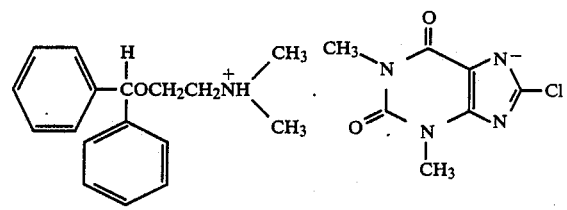

Dimenhydrinate

The term "ethylenediamine derivatives" as used herein refers to antihistaminic composition having structural formulas exemplified by, but not limited to, the following species:

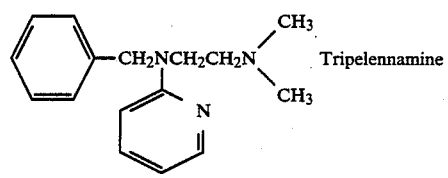

Tripelennamine

The term "alkylamine derivatives" as used herein refers to antihistaminic compositions having structural formulas exemplified by, but not limited to, the following species:

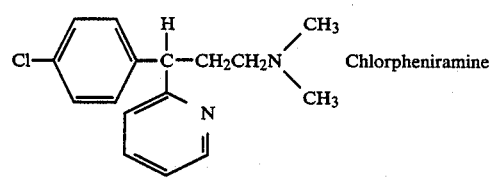

Chlorpheniramine

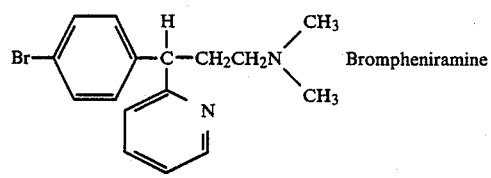

Brompheniramine

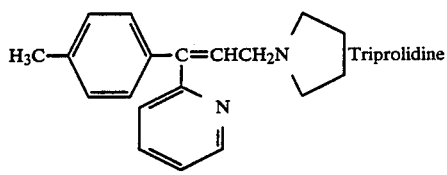

In vitro "zone of inhibition" screening has demonstrated that not all antihistamines included in the aforementioned three classes exhibit significant antimicrobial activity. It has been ascertained that at least the following compounds do exhibit such activity in vitro, and in vivo expanded flora testing has confirmed the antibacterial activity of some of these compounds while others remain to be tested:

Ethanolamine derivatives diphenhydramine, diphenhydramine hydrochloride and dimenhydrinate Ethylenediamine derivatives tripelennamine Alkylamine derivatives brompheniramine, chlorpheniramine and triprolidine All of the above antihistamines exhibited marked antibacterial activity and activity against *C. albicans*, but chlorpheniramine and triprolidine were ineffective against *T. mentagrophytes*. Pyrilamine, an alkylamine, showed activity against *T. mentagrophytes* but not the other pathogens screened.

A more preferred concentration range for the active antihistaminic agents used in the compositions and methods of the present invention is from about 1% to about 3% by weight. Numerous antihistamines of the classes mentioned above were found in vitro antibacterial testing, however to have minimum inhibitory concentrations as low as 0.25% (diphenhydramine), 0.5% (dimenhydrinate) and 0.5–1% (e.g., tripelennamine, brompheniramine and triprolidine).

The compositions utilized in the methods of the present invention for effecting local anti-infective treatment include conventional pharmaceutically acceptable vehicles which are suitable for topical use and chemically compatible with the active antihistamine ingredients. Such topical preparations containing, e.g., 2% of an antihistamine such as diphenhydramine hydrochloride are currently available in the form of lotions, aerosol sprays, creams and the like. Several specific examples of formulations suitable for use in the methods of the invention are set forth below.

The topical antihistamine-containing compositions suitable for use in the present invention may be employed on any tissue area where the anti-pruritic, anti-edema, anti-erythema and anti-inflammatory properties of the antihistaminic ingredient, as well as the newly discovered topical antibacterial and/or antimycotic properties, are required. Examples of such tissue areas include, but are by no means limited to, skin areas affected by insect bites, hives, poison ivy, allergic dermatoses, itching lesions, pustules and the like, ringworm, athlete's foot, thrush, etc., wherein pruritis, erythema and edema can be relieved by the antihistamine, and infection, particularly infection which may be exacerbated by dirt or scratching, can be prevented by the antibacterial properties of the active ingredient. Lotions, creams, gels and aerosol sprays are particularly suited for application to such affected skin areas. In addition, liquid solutions and sprays containing from about 0.5% to about 5% of the subject antihistaminic agents can be of great value when applied topically to infected, inflamed or fungally infested vaginal and perianal areas or the mouth, throat and nasal passages, acting to combat local infection as well as to provide the known antihistaminic effects of such agents. Isotonic sterile solutions of the antibacterially active antihistamines may be used to treat conjunctivitis and other inflammatory conditions of the eye.

The low toxicity of the selected antihistaminic agents makes them suitable for use on the mucosa of the nose, mouth and throat, or in the eyes, where conventional topical antibacterial agents such as povidone iodine or benzoyl peroxide could not be used.

The amount of antihistamine-containing composition that must be applied to a particular tissue area to achieve the desired anti-infective effect may vary depending on the nature of the condition affecting the tissue area, the size of the tissue area and the frequency of application of the composition. Generally, compositions suitable for use in the methods of the present invention may be liberally applied to the affected areas from one to five times daily, with each application comprising from 0.1–100 mg of composition (i.e., antihistamine in vehicle) per square centimeter of tissue area.

The anti-infective treatment methods of the present invention utilizing antihistamine-containing compositions provide unique advantages. By the application of these topical compositions, both anti-infective effects and the various conventionally known effects of antihistamines can be achieved with a single preparation containing a single active ingredient known to be safe for topical use with few, if any, adverse side effects. These novel methods make the treatment of tissue areas requiring both anti-infective and antihistaminic therapy less expensive for health professionals and patients alike and enable the use of one topical medication in many first aid situations wherein it was previously believed that both a topical antihistamine (e.g., for relief of pruritus and swelling) and an antibacterial agent (to prevent infection) were required.

It has also been found that certain antihistaminic agents act synergistically with bactericidal alcohols (e.g. ethyl and isopropyl alcohol) to produce antimicrobial activity greater than can be achieved by either agent alone. Examples of gel vehicles containing 60 to 90% ethyl alcohol admixed with 2% diphenhydramine hydrochloride are disclosed in co-pending and commonly owned application Ser. No. 130,445, and those disclosures are incorporated herein by reference.

The compositions utilized in the methods of the present invention are generally self-preserving, i.e., they do not require added preservatives to retard spoilage because of the antibacterial activity of the antihistaminic active ingredients.

The following examples provide detailed illustrations of the anti-infective treatment methods of the present invention as well as compositions suitable for use in such methods. Moreover, in vitro and in vivo data demonstrating the antibacterial effectiveness of the compositions used in the invention are set forth. These examples are not intended, however, to limit or restrict the scope of the invention in any way, and should not be construed as providing methods, conditions, ingredients or starting materials which must be utilized exclusively to practice the present invention.

EXAMPLES 1–5

Antimicrobial Gels

The following ingredients were admixed to form homogeneous gels containing from 0.5 to 5.0% by weight of antihistamine (all percentages given are w/w):

| Ingredients | Ex. 1 | Ex. 2 | Ex. 3 | Ex. 4 | Ex. 5 |
|---|---|---|---|---|---|
| CARBOPOL 940 (carboxyvinyl polymer, B. F. Goodrich Chemical Co.) | 1.0% | 1.0% | 1.0% | 1.0% | 1.0% |
| NATROSAL 250 HHF (hydroxyethyl cellulose, Hercules, Inc.) | 0.2% | 0.2% | 0.2% | 0.2% | 0.2% |
| CERAPHYL 41 ($C_{12-15}$ alcohols lactate, Van Dyk & Co.) | 2.5% | 2.5% | 2.5% | 2.5% | 2.5% |
| Glycerine | 2.5% | 2.5% | 2.5% | 2.5% | 2.5% |
| QUADROL POLYOL (tetrahydroxy-propyl ethylenediamine, BASF Wyandotte Corp.) | 2.7% | 2.7% | 2.7% | 2.7% | 2.7% |
| COSMEDIA (polyacrylamidomethyl propane sulfonic acid, Henkel Corp.) | 2.0% | 2.0% | 2.0% | 2.0% | 2.0% |
| FD & C Blue No. 1, 10% sol. | 0.05% | 0.05% | 0.05% | 0.05% | 0.05% |
| Triethanolamine | 0.24% | 0.24% | 0.24% | 0.24% | 0.24% |
| Diphenhydramine HCl | 0.5% | 1.0% | 2.0% | 2.5% | 5.0% |
| Purified water | 88.31% | 87.81% | 36.81% | 86.31% | 83.81% |

EXAMPLES 6–10

Antimicrobial Creams

The following ingredients were admixed to form homogeneous creams containing from 0.5 to 5.0% by weight of antihistamine:

| Ingredients | Ex. 6 | Ex. 7 | Ex. 8 | Ex. 9 | Ex. 10 |
|---|---|---|---|---|---|
| AMERCHOL L-101 (Mineral oil and multi-stearyl extract, American Cholesterol Products, Inc.) | 5.0% | 5.0% | 5.0% | 5.0% | 5.0% |
| Isopropyl Palmitate | 4.0% | 4.0% | 4.0% | 4.0% | 4.0% |
| CERASYNT PA (Propylene glycol stearate, Van Dyk & Co.) | 7.0% | 7.0% | 7.0% | 7.0% | 7.0% |
| Cetyl Alcohol | 2.5% | 2.5% | 2.5% | 2.5% | 2.5% |
| ARLACEL 60 (Sorbitan monostearate, ICI Americas, Inc.) | 2.0% | 2.0% | 2.0% | 2.0% | 2.0% |
| Sorbic Acid | 0.2% | 0.2% | 0.2% | 0.2% | 0.2% |
| TWEEN 60 (Polysorbate 60, ICI Americas, Inc.) | 3.0% | 3.0% | 3.0% | 3.0% | 3.0% |
| MYRJ 52 (Polyoxyl 40 stearate, ICI Americas, Inc.) | 1.0% | 1.0% | 1.0% | 1.0% | 1.0% |
| Propylene Glycol | 8.0% | 8.0% | 8.0% | 8.0% | 8.0% |
| Purified Water | 66.8% | 66.3% | 65.3% | 64.8% | 62.3% |
| Diphenhydramine HCl | 0.5% | 1.0% | 2.0% | 2.5% | 5.0% |

EXAMPLES 11–15

Antimicrobial Lotions

The following ingredients were admixed to form homogeneous lotions containing from 0.5 to 5.0% by weight of antihistamine:

| Ingredients | Ex. 11 | Ex. 12 | Ex. 13 | Ex. 14 | Ex. 15 |
|---|---|---|---|---|---|
| AMERCHOL L-101 (Mineral oil and multi-stearyl extract, American Cholesterol Products, Inc.) | 21.0% | 21.0% | 21.0% | 21.0% | 21.0% |
| Isopropyl Palmitate | 1.5% | 1.5% | 1.5% | 1.5% | 1.5% |
| CERASYNT PA (Propylene glycol stearate, Van Dyk & Co.) | 3.0% | 3.0% | 3.0% | 3.0% | 3.0% |
| Cetyl Alcohol | 1.5% | 1.5% | 1.5% | 1.5% | 1.5% |
| ARLACEL 60 (Sorbitan monostearate, ICI Americas, Inc.) | 1.0% | 1.0% | 1.0% | 1.0% | 1.0% |
| TWEEN 60 (Polysorbate 60, ICI Americas, Inc.) | 1.5% | 1.5% | 1.5% | 1.5% | 1.5% |
| Sorbic Acid | 0.2% | 0.2% | 0.2% | 0.2% | 0.2% |
| MYRJ 52 (Polyoxyl 40 stearate, ICI Americas, Inc.) | 0.5% | 0.5% | 0.5% | 0.5% | 0.5% |
| Propylene Glycol | 2.0% | 2.0% | 2.0% | 2.0% | 2.0% |
| Purified Water | 67.3% | 66.8% | 65.8% | 65.3% | 62.8% |
| Diphenhydramine HCl | 0.5% | 1.0% | 2.0% | 2.5% | 5.0% |

EXAMPLE 16

Antimicrobial Isotonic Solutions

An isotonic solution of sodium chloride in sterile preserved water was prepared containing 2% diphenhydramine hydrochloride by weight.

EXAMPLE 17

Alternative Antimicrobial Gels Creams, Lotions and Solutions

Gels, creams, lotions and solutions may be prepared in accordance with Examples 1–16, substituting in place of diphenhydramine hydrochloride the following antihistaminic agents:

0.5–5% dimenhydrinate hydrochloride
0.5–5% tripelennamine citrate
0.5–5% brompheniramine maleate
0.5–5% chlorpheniramine maleate
0.5–5% triprolidine hydrochloride Suitable minor changes in the nature and quantities of the inactive ingredients comprising the gel, cream and lotion vehicles may be required n certain cases with the above substitute active ingredients. In general, the vehicles set forth in Examples 1–16 are suitable for most of the antibacterially active antihistaminic agents.

EXAMPLE 18

Method of Anti-Infective Treatment for Skin Areas

A sufficient quantity of a gel, cream or lotion according to Examples 1–15 to coat a skin area requiring anti-infective treatment is applied directly to the skin area and gently spread until a thin, uniform coating over the affected area is achieved. This treatment can be repeated from 1–5 times daily, as required.

EXAMPLE 19

Method of Providing Anti-Infective Treatment to the Nose and Throat 30 ml. of an isotonic solution prepared according to Example 16 are placed in a squeezable spray bottle with a nebulizer tip. The solution is then sprayed directly onto an inflamed nasal passages by inserting the tip of the container into the nostrils and squeezing the container, or sprayed onto inflamed throat area by inserting the tip into the mouth, directed toward the throat, and squeezing the container. This treatment can be repeated from 1–5 times daily as required.

EXAMPLE 20

Method of Providing Anti-Infective Treatment to the Conjunctiva

One or two drops of a sterile isotonic solution prepared according to Example 16 are administered directly into the eye with an eyedropper for treatment of conjunctivitis.

EXAMPLE 21

In Vitro Screening

A. Antibacterial Activity

The following antihistamines in liquid solution were screened for in vitro antibacterial activity:

Ethanolamine Derivatives (a) Diphenhydramine 2% aqueous solution
(b) Dimenhydrinate 2% aqueous solution
(c) Doxylamine 2% aqueous solution

Ethylenediamine Derivatives (a) Pyrilamine 2% aqueous solution
(b) Tripelennamine 2% aqueous solution

Alkylamine Derivatives (a) Brompheniramine 2% aqueous solution
(b) Chlorpheniramine 2% aqueous solution
(c) Triprolidine 2% aqueous solution The 2% solutions listed above were diluted further with sterile water, using serial half-step dilutions. Forty lambda of each were then pipetted onto seeded Mueller-Hinton agar plates. The agar plates were then incubated for 24 hours at 35° C. and zones of inhibition were then recorded. The Minimum Inhibitory Concentration (MIC) was the lowest concentration of the test material which produced a zone of inhibition against the organism. The MIC for each test material (antihistamine), using each organism, is listed in Table 1.

Preparation of Mueller-Hinton agar plates:

Stock cutaneous strains of each organism were grown in Mueller-Hinton broth for 18 hours at 35° C. Plates were seeded with the 18 hour broth culture, allowed to air dry at room temperature (about 10 minutes) and then used for determination of zones of inhibition as outlined above.

TABLE 1

Minimum Inhibitory Concentrations (mg/ml) of Several Antihistamines on Cutaneous Bacteria*

| Antihistamine: | Rank Order** | ML | SA | CM | EC | PA |
|---|---|---|---|---|---|---|
| Diphenhydramine | 1 | 2.5 | 2.5 | 2.5 | 2.5 | 5.0 |
| Brompheniramine | 2 | 5.0 | 10.0 | 3.0 | 5.0 | 10.0 |
| Chlorpheniramine | 2 | 5.0 | 10.0 | 5.0 | 5.0 | 10.0 |
| Triprolidine | 3 | 10.0 | 10.0 | 5.0 | 5.0 | 10.0 |
| Dimenhydrinate | 3 | 10.0 | 10.0 | 5.0 | 5.0 | 10.0 |
| Tripelennamine | 3 | 10.0 | 10.0 | 5.0 | 5.0 | 10.0 |
| Pyrilamine | 4 | 0 | 0 | 10.0 | 10.0 | 0 |
| Doxylamine | 5 | 0 | 0 | 0 | 0 | 0 |

*ML = Micrococcus luteous
SA = Staphylococcus aureus
CM = Corenybacterium minutissimum
EC = Escherichia coli
PA = Pseudomonas aeroginosa
**Rank - highest inhibition (rank 1) to lowest (rank 5)

B. Antimycotic Activity

A laboratory propagated strain of *C. albicans*, originally isolated from an infected skin lesion of a patient, was grown in Mueller-Hinton broth for 18 hours at 35° C. Plates were then seeded with the broth culture and allowed to air-dry at room temperature (22° C.) for about 10–15 minutes. Forty lambda of the 2% aqueous solutions or of serial half-step dilutions in water were then pipetted onto the seeded Mueller-Hinton agar plates. The plates were then incubated for 24 hours at 35° C. and zones of inhibition were then recorded. The Minimum Inhibitory Concentration (MIC) was the lowest concentration of the test material which produced a zone of inhibition against the organism. The MIC for each test material (antihistamine) is listed in the enclosed table. Table 2 lists the MIC's against *C. albicans* while Table 3 lists the MIC's against in vitro-grown spores of the human pathogen *T. mentagrophytes*. This strain was isolated from a human infection and was grown on Sabourand-Dextrose agar for 2 weeks. The spores were collected by flooding the agar plates after the 2 week growth period with a 0.01% solution of Tween-80 (sorbitol ester) and then filtering the Tween solution through gauze mesh to collect the suspension of spores. Sabourand-Dextrose agar plates are then seeded with the spore suspension. After air-drying, 40 lambda of each test solution is pipetted onto the plates and the plates left to incubate for 4 days at 22° C.

TABLE 2

Minimum Inibitory Concentrations (MIC's) of Several Aqueous Antihistamines on *C. albicans**

| ANTIHISTAMINE | MIC (mg/ml) |
|---|---|
| Diphenhydramine | 10 |
| Brompheniramine | 20 |
| Chlorpheniramine | 20 |
| Triprolidine | 20 |
| Dimenhydrinate | 20 |
| Tripelennamine | 20 |

TABLE 2-continued

Minimum Inibitory Concentrations (MIC's) of
Several Aqueous Antihistamines on *C. albicans*\*

| ANTIHISTAMINE | MIC (mg/ml) |
|---|---|
| Pyrilamine | No inhibition |
| Doxylamine | No inhibition |

\**C. albicans:* A human pathogenic yeast responsible for thrush and diaper rashes in infants and for moniliasis (vaginal) and human skin infections in adults.

TABLE 3

Minimum Inhibitory Concentrations (MIC's) of
Several Aqueous Antihistamines Against
Spores of *T. Mentagrophytes*\*

| ANTIHISTAMINE | MIC (mg/ml) |
|---|---|
| Diphenhydramine | 10 |
| Brompheniramine | 20 |
| Chlorpheniramine | No inhibition |
| Triprolidine | No inhibition |
| Dimenhydrinate | 20 |
| Tripelennamine | 20 |
| Pyrilamine | 20 |
| Doxylamine | No inhibition |

\**T. mentagrophytes:* A human pathogenic fungus responsible for ringworm, athlete's foot and chronic fungal infections in susceptible humans.

EXAMPLE 22

In Vivo Antibacterial Tests

A. Expanded Flora Test—Bactericidal Activity

Test material A & B (both gels) were prepared with the following ingredients:

| Ingredient | Material A | Material B |
|---|---|---|
| CARBOPOL 940 (carboxyvinyl polymer) | 1.0% | 1.0% |
| NATROSAL 250 HHF (hydroxyethyl cellulose) | 0.2% | 0.2% |
| Purified Water | 28.75% | 86.71% |
| CERAPHYL ($C_{12-15}$ alcohols lactate) | 2.5% | 2.5% |
| Glycerin | 2.5% | 2.5% |
| QUADROL POLYOL (tetrahydroxypropul ethylenediamine) | 2.7% | 2.7% |
| UVINUL MS-40 (benzophenone) | 0.1% | 0.1% |
| Diphenhydramine HCl | — | 2.0% |
| Alcohol USP | 60.0% | — |
| FDC Blue #1 1% Sol. | 0.05% | 0.05% |
| COSMEDIA (polyacrylamidomethylpropane sulfonic acid) | 2.0% | 2.0% |
| Triethanolamine | 0.2% | 0.24% |

As indicated, the only difference between the two test materials was that material A contained about 60% ethyl alcohol by weight and Material B contained no alcohol but about 2% diphenhydramine by weight.

The floral expansion was carried out by translocating cutaneous microflora from the perineal region to the forearms of 10 subjects and then expanding them by covering the forearm sites occlusively under chambers for 24 hours. After that, materials A and B were applied in duplicate to designated test sites and the sites cultured at (i) 5 minutes and (ii) 10 minutes for quantitative bacteriology. A control (untreated site) was included at each time-point.

The findings are summarized in Table 4. There was a highly significant killing effect by both the alcohol gel (A) and the diphenhydramine gel (B) at both time-points. There were no apparent significant differences in bactericidal activity between A and B, however, either at 5 or at 10 minutes. On the average, both treatments (A and B) produced two to three orders of magnitude reduction in bacterial counts (e.g., from $10^6$ organisms per $cm^2$ to $10^{3.5}$ organisms per $cm^2$).

TABLE 4

$Log_{10}$ of Aerobic Bacteria Per $CM^2$ of Skin Surface
At 5.0 and 10.0 Minutes After Drug Application

| Subject Number: | 5.0 Minutes | | | 10.0 Minutes | | |
|---|---|---|---|---|---|---|
| | Control | A | B | Control | A | B |
| 1 | 5.61 | 2.37 | 2.11 | 5.74 | 2.53 | 3.23 |
| 2 | 5.46 | 1.89 | 2.16 | 5.58 | 1.81 | 0 |
| 3 | 6.07 | 2.96 | 2.96 | 5.37 | 3.37 | 4.32 |
| 4 | 6.02 | 3.32 | 5.29 | 6.02 | 4.07 | 5.26 |
| 5 | 6.34 | 4.32 | 5.16 | 6.26 | 5.26 | 5.26 |
| 6 | 6.56 | 2.67 | 1.11 | 6.11 | 4.11 | 5.42 |
| 7 | 6.39 | 3.73 | 4.16 | 6.23 | 2.74 | 4.59 |
| 8 | 6.26 | 4.26 | 5.42 | 6.68 | 4.23 | 4.44 |
| 9 | 6.11 | 0 | 3.89 | 6.16 | 2.72 | 3.11 |
| 10 | 6.07 | 3.89 | 3.42 | 6.11 | 4.26 | 3.29 |

B. Expanded Flora Test—Bacteriostatic Activity (24 Hour)

The method described above was repeated on 6 new subjects with test materials A and B, but quantitative bacterial values were taken after 24 hours on the treated or control sites to assay for aacteriostatic activity. Additional test materials C, D, E and F were also applied to the forearms of these subjects for comparative purposes. These materials comprised the following:

Material C: The same ingredients as material A with the addition of 2% diphenhydramine in place of 2% purified water—i.e., this gel contained both 60% ethyl alcohol and 2% diphenhydramine.

Material D: Bacitracin ointment U.S.P. (500 units per gram).

Material E: 60% ethyl alcohol (liquid).

Material F: Povidone iodine ointment U.S.P. 10%.

As a control, a material designated "base" containing the same ingredients as materials A, B and C but no alcohol or diphenhydramine was applied to the patient's forearms as well. In addition, an untreated site was cultured for control purposes.

The findings are summarized in Table 5. There was a highly significant bacteriostatic effect observed with both materials A and B, considerably superior to the effect achieved with bacitracin (material D) or ethyl alcohol (material E). But a substantially greater bacteriostatic effect was observed with material C, close to that of povidone iodine (material F), indicating a synergistic interaction between the antihistamine and alcohol components of material C.

TABLE 5

$Log_{10}$ of Aerobic Bacteria Per $CM^2$ of Skin Surface
At 24 Hours After Drug Application

| | Base | Untreated | A | B | C | D | E | F |
|---|---|---|---|---|---|---|---|---|
| 1 | 6.85 | 6.93 | 5.11 | 3.34 | 3.07 | 6.26 | 6.91 | 2.81 |
| 2 | 6.99 | 6.97 | 5.26 | 1.59 | 2.32 | 6.29 | 6.89 | 1.59 |
| 3 | 7.01 | 6.95 | 3.16 | 4.72 | 2.59 | 6.53 | 4.42 | 1.11 |
| 4 | 6.76 | 6.55 | 4.26 | 4.96 | 1.59 | 6.26 | 5.81 | 2.89 |
| 5 | 7.01 | 6.83 | 5.71 | 1.42 | 1.42 | 5.56 | 6.85 | 1.42 |
| 6 | 6.93 | 6.89 | 2.29 | 1.59 | 1.81 | 5.96 | 6.91 | 0 |

It should be noted that the antimicrobial treatment methods of the present invention utilizing antihistamine-containing compositions are not limited to the treatment of conditions where both antihistaminic and antibacterial or antimycotic treatment are required. The compositions and methods of the invention are useful in treating any tissue areas where topical antibacterial or antimycotic agents would normally be applied for anti-infective purposes, whether or not pruritus, erythema or edema are present. In fact, as demonstrated by the in vivo data set forth above, the compositions utilized in the subject methods are better and more potent antibacterial agents than many drugs commonly used as the principal active ingredients in commercially available topical anti-infective products which have no antihistaminic components.

As further demonstrated by the clinical data, te methods of the invention provide not merely a short-term bactericidal effect to the treated tissue areas, but also a long-term bacteriostatic effect, thus inhibiting re-infection of the treated areas.

It has thus been shown that there are provided compositions and methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense

What is claimed as new and desired to be protected by Letters Patent is set forth in the following claims.

1. A method of providing local antimycotic treatment to a human or animal tissue area, in need thereof, comprising applying to said tissue area of an effective amount of a composition containing (a) from about 0.5 to about 5.0% by weight of an antihistaminic agent selected from the group consisting of ethanolamine derivatives and pharmaceutically acceptable salts thereof, and (b) a pharmaceutically acceptable topical vehicle.

2. A method according to claim 1 wherein said composition contains from about 1.0 to about 3.0% by weight of said antihistaminic agent.

3. A method according to claim 1 wherein said ethanolamine derivative is selected from the group consisting of diphenhydramine, dimenhydrinate and pharmaceutically acceptable salts thereof.

4. A method according to claim 3 wherein said vehicle ethanolamine derivative is diphenhydramine hydrochloride.

5. A method according to claim 1 wherein said vehicle is a gel.

6. A method according to claim 1 wherein said vehicle is a cream.

7. A method according to claim 1 wherein said vehicle is a lotion.

8. A method according to claim 1 wherein said vehicle is a liquid.

9. A method according to claim 8 wherein said liquid is an isotonic solution in which the antihistaminic agent is dissolved.

10. A method according to claim 1 wherein said effective amount is from 0.1 to 100 mg. of the composition per square centimeter of tissue area.

11. A method according to claim 1 wherein the composition is applied to the tissue area in a sufficient amount to provide a thin coating of composition over the area.

12. A method according to claim 1 wherein said composition is applied to the tissue area from 1–5 times daily.

13. A method according to claim 1 wherein said tissue area is an area of the skin, vagina, perianal area, nasal passages, throat or eyes.

14. A method according to claim 1 wherein said topical vehicle is selected from the group consisting of liquids, lotions, creams, and gels.

* * * * *